(12) United States Patent
Arima (10) Patent No.: US 10,624,605 B2
(45) Date of Patent: Apr. 21, 2020

(54) RADIATION IMAGING CONTROL APPARATUS, METHOD OF CONTROLLING THE SAME, AND NON-TRANSITORY COMPUTER-READABLE STORAGE MEDIUM

(71) Applicant: CANON KABUSHIKI KAISHA, Tokyo (JP)

(72) Inventor: Keisuke Arima, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 275 days.

(21) Appl. No.: 15/481,629

(22) Filed: Apr. 7, 2017

(65) Prior Publication Data

US 2017/0296135 A1   Oct. 19, 2017

(30) Foreign Application Priority Data

Apr. 19, 2016  (JP) .................................. 2016-083854

(51) Int. Cl.
*A61B 6/00* (2006.01)
*G06F 19/00* (2018.01)

(52) U.S. Cl.
CPC ................ *A61B 6/582* (2013.01); *A61B 6/52* (2013.01); *A61B 6/54* (2013.01); *G06F 19/321* (2013.01)

(58) Field of Classification Search
CPC .. A61B 6/00; A61B 6/582; A61B 6/52; A61B 6/54; A61B 6/58; A61B 6/461; A61B 6/463; A61B 6/465; G06F 19/00; G06F 19/321
USPC ................................ 378/62, 98.2, 98.5, 207
See application file for complete search history.

(56) References Cited

U.S. PATENT DOCUMENTS

| | | | |
|---|---|---|---|
| 10,206,642 B2 | 2/2019 | Hiroike | |
| 2004/0227821 A1* | 11/2004 | Matsuno | G06F 19/321 348/207.99 |
| 2007/0036268 A1 | 2/2007 | Matsuno | 378/98.2 |
| 2010/0169833 A1 | 7/2010 | Arima | 715/821 |
| 2011/0208048 A1 | 8/2011 | Arima | 600/436 |

FOREIGN PATENT DOCUMENTS

| | | |
|---|---|---|
| JP | 2004-337232 | 12/2004 |
| JP | 4764098 | 6/2011 |
| JP | 2015-173804 | 10/2015 |
| WO | 2014/208722 | 12/2014 |

* cited by examiner

*Primary Examiner* — Jurie Yun
(74) *Attorney, Agent, or Firm* — Venable LLP (57) ABSTRACT

A radiation imaging control apparatus comprises an obtainment unit configured to obtain a radiation image captured by an image capturing unit; an extraction unit configured to extract, as a diagnostic image for comparison, a radiation image re-captured by the image capturing unit in a case in which the radiation image is a rejected image; and an output unit configured to output the rejected image and the diagnostic image for comparison to an external apparatus.

21 Claims, 8 Drawing Sheets

FIG. 2A

| | | | | | |
|---|---|---|---|---|---|
| PATIENT NAME: | | | | | |
| DATE OF BIRTH: / / | AGE: | | | [CONFIRM] | |
| PATIENT ID: | | SEX: ○MALE ○FEMALE ○OTHER | | | |

| EXAMINATION | PATIENT | PATIENT NAME | SEX | DATE OF BIRTH | AGE |
|---|---|---|---|---|---|
| 0001 | P333 | GANON SABURO | MALE | 1981/11/11 | 29 |
| 0002 | P222 | GANON JIRO | MALE | 2002/2/2 | 7 |
| 0003 | P111 | GANON TARO | MALE | 2001/1/10 | 8 |
| 0004 | P777 | GANON HANAKO | FEMALE | 1977/7/7 | 12 |
| 0005 | P123 | GANON ICHIRO | MALE | 2003/3/3 | 3 |
| 0006 | P444 | GANON SHIRO | MALE | 1964/4/4 | 45 |
| 0007 | P555 | GANON GORO | MALE | 1955/5/5 | 54 |
| 0008 | P666 | GANON ROKURO | MALE | 1976/6/6 | 33 |
| | | | | | |
| | | | | | |
| | | | | | |

PATIENT NAME:
PATIENT ID:
DATE OF BIRTH:
AGE:
SEX:

EXAMINATION ID:

[IMAGING INFORMATION INPUT]   [EXAMINATION START]

FIG. 2B

| | | PATIENT NAME: | | | | |
|---|---|---|---|---|---|---|
| | | DATE OF BIRTH: / / | AGE: | | | |
| | | PATIENT ID: | SEX: ○MALE ○FEMALE ○OTHER | | | CONFIRM |

| EXAMINATION | PATIENT | PATIENT NAME | SEX | DATE OF BIRTH | AGE |
|---|---|---|---|---|---|
| O001 | P333 | GANON SABURO | MALE | 1981/11/11 | 29 |
| O002 | P222 | GANON JIRO | MALE | 2002/2/2 | 7 |
| O003 | P111 | GANON TARO | MALE | 2001/1/10 | 8 |
| O004 | P777 | GANON HANAKO | FEMALE | 1977/7/7 | 12 |
| O005 | P123 | GANON ICHIRO | MALE | 2003/3/3 | 3 |
| O006 | P444 | GANON SHIRO | MALE | 1964/4/4 | 45 |
| O007 | P555 | GANON GORO | MALE | 1955/5/5 | 54 |
| O008 | P666 | GANON ROKURO | MALE | 1976/6/6 | 33 |

PATIENT NAME: GANON TARO
PATIENT ID: P111
DATE OF BIRTH: 2001/1/10
AGE: 8
SEX: MALE

EXAMINATION ID: O003

| FRONT OF CHEST | SENSOR A |
| SIDE OF CHEST | SENSOR A |

IMAGING INFORMATION INPUT    EXAMINATION START

FIG. 4

| IMAGE ID | EXAMINATION ID | IMAGING METHOD ID | IMAGING METHOD NAME | SERIES ID | REJECTED IMAGE |
|---|---|---|---|---|---|
| I-0001 | O-0001 | P-0001 | FRONT OF CHEST | S-0001 | Yes |
| I-0002 | O-0001 | P-0001 | FRONT OF CHEST | S-0001 | No |
| I-0003 | O-0001 | P-0002 | SIDE OF CHEST | S-0002 | No |
| I-0004 | O-0002 | P-0003 | FRONT OF ABDOMEN | S-0003 | Yes |
| I-0005 | O-0002 | P-0003 | FRONT OF ABDOMEN | S-0004 | No |

| IMAGE ID | CONTRAST | ANNOTATION POSITION | ANNOTATION CHARACTER STRING | CUTOUT | ROTATION |
|---|---|---|---|---|---|
| I-0001 | 1 | | | (0, 0), (1, 1) | 0 |
| I-0002 | 2 | (0.1, 0.2) | R | (0.2, 0.2), (0.8, 0.8) | 0 |
| I-0003 | 3 | | | (0.3, 0.3), (0.7, 0.7) | 180 |
| I-0004 | 1 | | | (0, 0), (1, 1) | 0 |
| I-0005 | 3 | (0.8, 0.1) | L | (0.3, 0.3), (0.7, 0.7) | 90 |
| ⋮ | ⋮ | ⋮ | ⋮ | ⋮ | ⋮ |

RADIATION IMAGING CONTROL APPARATUS, METHOD OF CONTROLLING THE SAME, AND NON-TRANSITORY COMPUTER-READABLE STORAGE MEDIUM

BACKGROUND OF THE INVENTION

Field of the Invention

The present invention relates to a radiation imaging control apparatus, a method of controlling the same, and a non-transitory computer-readable storage medium.

Description of the Related Art

Conventionally, in a radiography examination for the purpose of medical diagnosis, re-imaging may be necessary due to an imaging failure. The cause of re-imaging can be diverse as an imaging condition defect, a movement of a body, and positioning. An image which caused the re-imaging has an adverse influence and is discarded as a rejected image without being used for diagnosis.

Re-imaging not only exposes a patient to radiation but also brings loss of work time to a radiological technician and loss of trust toward a facility. Hence, for the purpose of reducing re-imaging, information related to failed imaging is being accumulated to perform a failure cause analysis and to consider measures against the failure. A captured image is generally output to PACS (Picture Archiving and Communication Systems). Some facilities have installed PACS for the purpose of accumulating rejected images and are becoming equipped with an environment for an imaging failure analysis. In Japanese Patent No. 4764098, there is disclosed a technique to increase the efficiency of rejected image accumulation by transmitting a rejected image to an output destination separate from that of a normal image which has not undergone re-imaging.

Also, in recent years, PACS that include a rejected image analysis function are being increasingly installed. In such a rejected image analysis system, not only an analysis by a rejected image alone is performed but also a comparative analysis with a diagnostic image serving as an example of successful imaging of the rejected image is performed.

However, the technique disclosed in Japanese Patent No. 4764098 is not capable of collecting a diagnostic image for comparison.

The present invention has been made in consideration to the above problem and provides a technique of collecting a rejected image and a diagnostic image for comparison suitable for the analysis of the rejected image.

SUMMARY OF THE INVENTION

According to one aspect of the present invention, there is provided a radiation imaging control apparatus comprising: an obtainment unit configured to obtain a radiation image captured by an image capturing unit; an extraction unit configured to extract, as a diagnostic image for comparison, a radiation image re-captured by the image capturing unit in a case in which the radiation image is a rejected image; and an output unit configured to output the rejected image and the diagnostic image for comparison to an external apparatus.

Further features of the present invention will become apparent from the following description of exemplary embodiments with reference to the attached drawings.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

<Arrangement of Radiation Imaging System>

Figure 1:
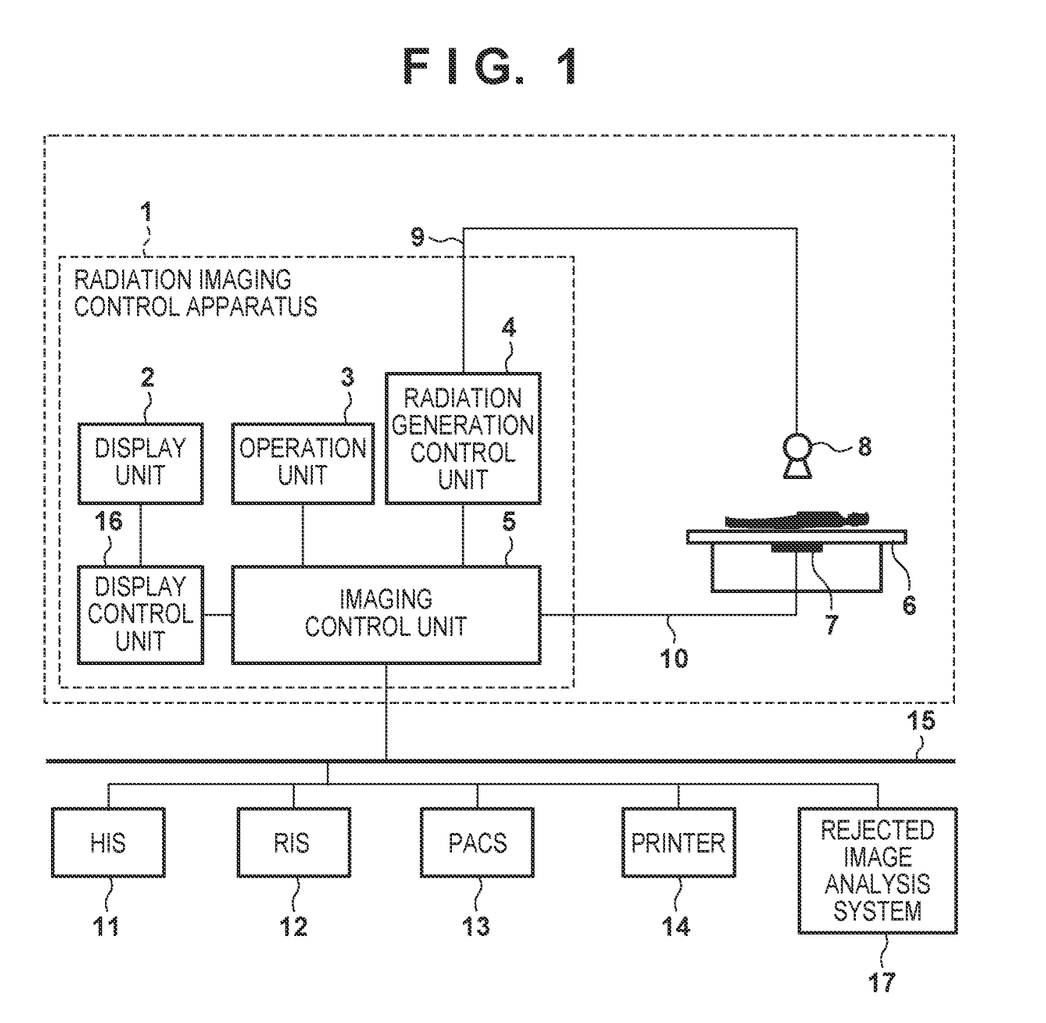
FIG. 1 is a view showing an example of the arrangement of a radiation imaging system according to an embodiment of the present invention.

FIG. 1 is a view showing an example of the arrangement of a radiation imaging system according to an embodiment of the present invention. The radiation imaging system includes a radiation imaging control apparatus 1 and an HIS (Hospital Information System) 11 that manages the progress of radiation imaging. The system also includes an RIS (Radiology Information System) 12, PACS (Picture Archiving and Communication Systems: an image server) 13, a printer 14, and a rejected image analysis system 17.

The HIS 11 may include a server that manages accounting information. When the necessity of radiation imaging is determined, an examination instruction is input from an HIS terminal and is transmitted to a radiology department which is the request destination. This request information is called an examination order. The examination order includes the department name of the request source, examination items, and personal data of a patient. When the radiology department receives an examination order via the RIS 12, imaging conditions are added to the examination order, and the order is transferred to the radiation imaging control apparatus 1. The radiation imaging control apparatus 1 performs radiation imaging in accordance with the received examination order. Examination information is added to the captured image, and transfer of the image to the PACS 13 and print output by the printer 14 are performed. Examination implementation information by the radiation imaging control apparatus 1 is also transferred to the HIS 11. The implementation information transferred to the HIS 11 is also used for, other than the progress management of the examination, an accounting process after the examination. In addition, a rejected image is transferred to a rejected image analysis system 17 in which the analysis of a rejected image is performed.

These apparatuses are connected by a network 15 formed from, for example, a LAN (Local Area Network) or a WAN (Wide Area Network). Note that these apparatuses include at least one or a plurality of computers. A computer is provided with, for example, a main control unit such as a CPU and storage units such as a ROM (Read Only Memory) and a RAM (Random Access Memory). The computer may also be provided with a communication unit such as a network card, and an input/output unit such as a keyboard, display, or a touch panel. These constitutive elements are connected by a bus and are controlled by the main control unit reading out and executing programs stored in the storage unit.

<Arrangement of Radiation Imaging Control Apparatus>

Here, the radiation imaging control apparatus 1 includes a display unit 2, an operation unit 3, a radiation generation control unit 4, an imaging control unit 5, and a display control unit 16.

The radiation generation control unit 4 is connected to a radiation generation unit 8 via a cable 9 and controls radiation irradiation from the radiation generation unit 8. The radiation generation unit 8 is implemented by, for example, a radiation tube and irradiates an object (for example, a specific portion of a patient) with radiation.

The operation unit 3 generally controls processing in the radiation imaging control apparatus 1. The display unit 2 is implemented by, for example, a liquid crystal display and displays various kinds of information to an operator (an imaging technician, a doctor, or the like). The operation unit 3 is implemented by, for example, a mouse or operation buttons and inputs various kinds of instructions from the operator to the apparatus. Note that the display unit 2 and the operation unit 3 may be implemented by a touch panel integrating these units.

The imaging control unit 5 is connected to a radiation detector 7 via a cable 10. Power, image signals, and control signals are exchanged between the imaging control unit and the radiation detector via the cable 10. The radiation detector 7 detects the radiation transmitted through the object and functions as a detector that obtains a radiation image based on the object. That is, a radiation imaging unit is implemented by a cooperative operation of the radiation generation unit 8 and the radiation detector 7. Note that the radiation detector 7 is set on a standing posture or supine posture imaging table 6.

The imaging control unit 5 functions as an instruction unit that instructs the start of a radiation imaging operation corresponding to at least one piece of order information received from the RIS 12. The order information includes, for example, subject information and one or a plurality of imaging portions regarding the subject. Here, a start instruction is instructed when the operation unit 3 receives user input. Alternatively, the imaging control unit 5 may select the order information of the imaging to be performed and instruct the start of imaging.

When imaging is performed, an image is displayed on the display unit 2. The operator can perform, via the operation unit 3, editing of an image such as image processing, cutout, addition of an annotation, and geometric conversion to the displayed image.

However, there is a case in which a so-called rejected image that is unsuitable for use in diagnosis is obtained due to an image blur caused by a movement of the subject or a failure to properly fix the posture. In the case of such imaging failure, re-imaging is performed to obtain an image suitable for diagnosis. A rejected image corresponding to the image obtained by re-imaging is displayed in the display unit 2 so that its unsuitability for diagnosis can be discriminated.

Subsequently, when all of the radiation imaging operations corresponding to the order information are finished and the user performs an input to confirm the completion of the order via the operation unit 3, the imaging control unit 5 transmits each diagnostic image to the PACS 13. The rejected image that caused the re-imaging and the diagnostic image obtained by the re-imaging are transmitted to the rejected image analysis system 17 which is an external apparatus.

In this manner, the rejected image as an analysis target and the diagnostic image serving as a comparison target in the rejected image analysis are transmitted to the rejected image analysis system 17. This contributes to improving the accuracy of the rejected image analysis.

An example of the arrangement of a radiation imaging system according to the embodiment of the present invention has been described above. Note that the arrangement shown in FIG. 1 is merely an example and may be appropriately changed. For example, although various kinds of apparatuses are connected to the radiation imaging control apparatus 1 via the network 15, the radiation imaging control apparatus 1 need not always be connected to these apparatuses. The rejected image and the diagnostic image may be output to a portable medium such as a DVD and input to the rejected image analysis system 17 via the portable medium. In addition, this network 15 may be formed as a wired network or may be partially formed by a wireless signal transmission path.

<Imaging Processing>

Here, a processing procedure of capturing a radiation image along the sequence of an examination by the radiation imaging system shown in FIG. 1 will be described.

Patient information and examination information are input to the radiation imaging control apparatus 1 upon receiving an examination request document or an examination request from the RIS 12. The patient information includes a patient name, a patient ID, and the like. The examination information includes imaging information defining the contents of the imaging to be performed on the patient.

Figure 2A:
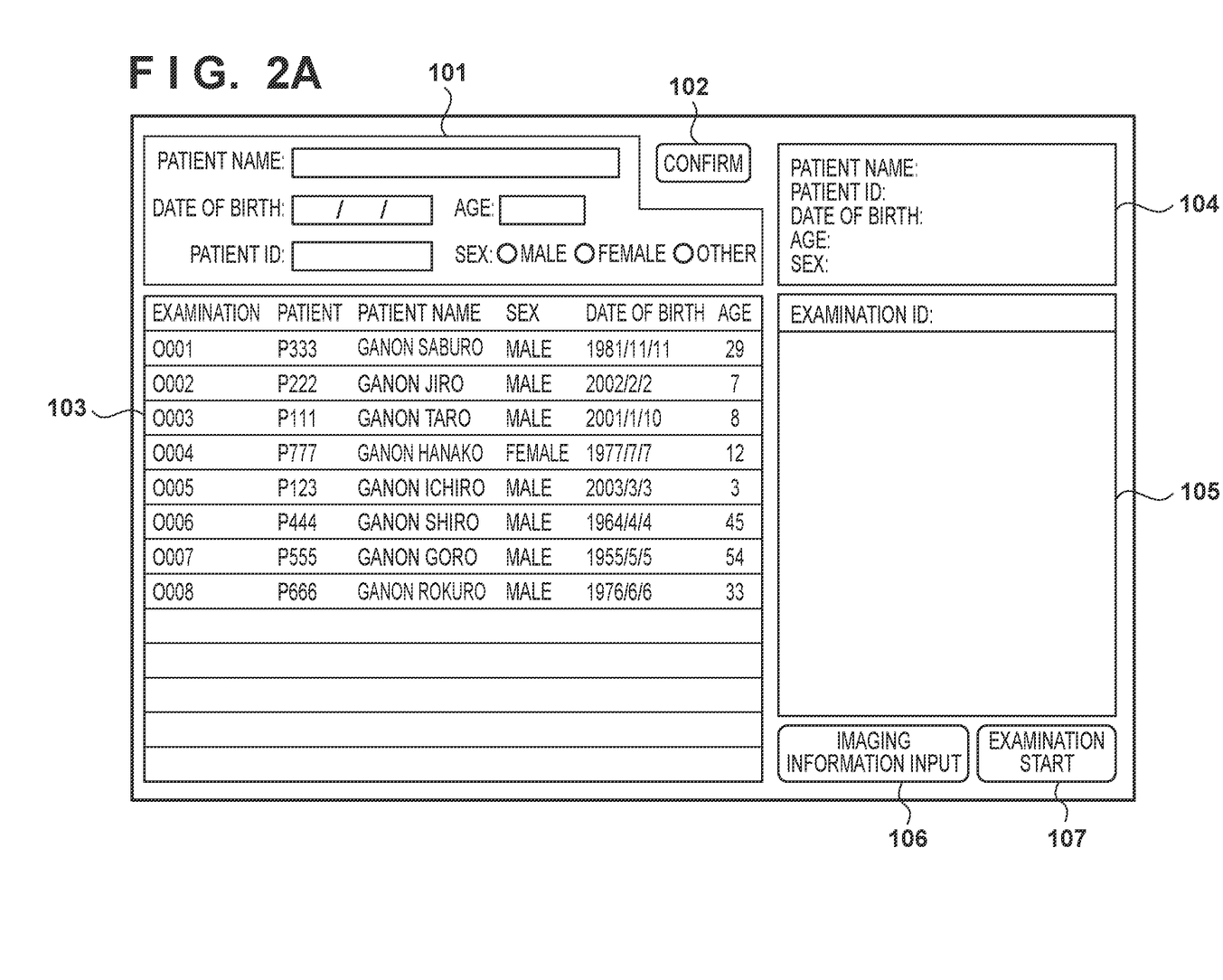
FIGS. 2A to 2C are views each showing an example of a new examination input screen according to the embodiment of the present invention.
Figure 2B:
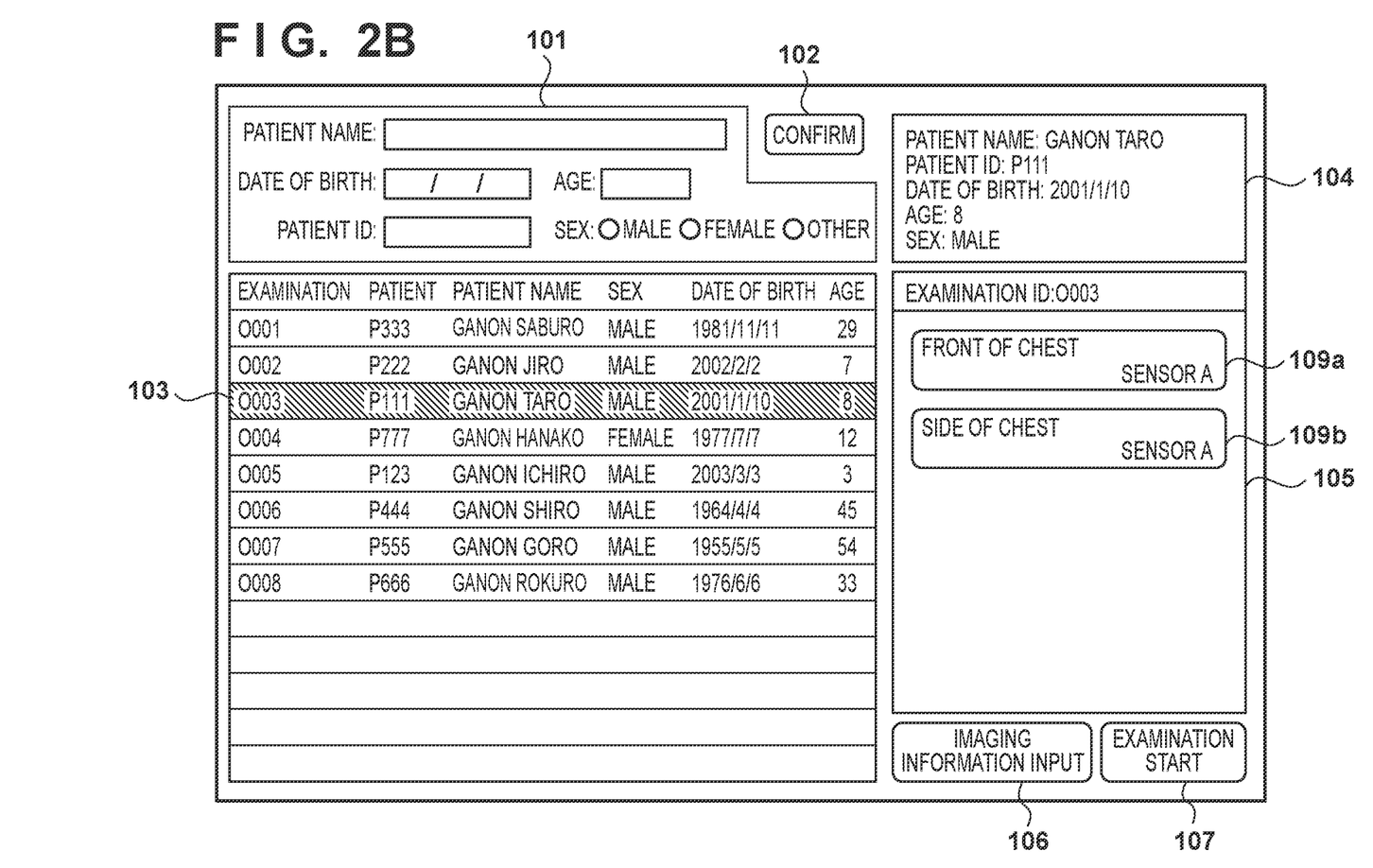
Figure 2C:
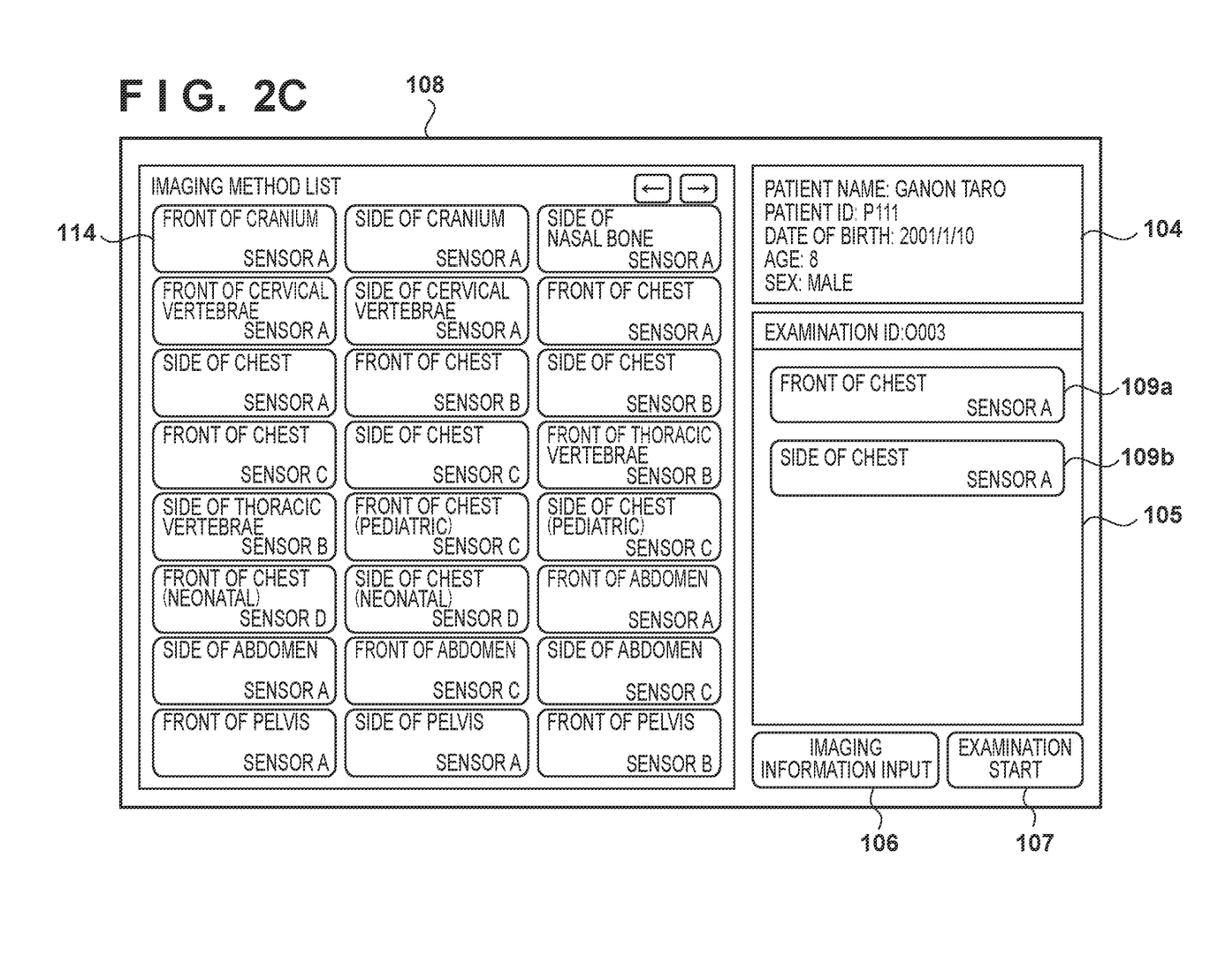

The radiation imaging control apparatus 1 displays, by the control of display control unit 16, a new examination input screen on the display unit 2 as shown in FIGS. 2A to 2C. As shown in FIG. 2A, the new examination input screen includes a patient information input region 101, a patient information confirmation button 102, and a requested examination list 103. The new examination input screen also includes a patient information display region 104, an imaging information display region 105, an imaging information input button 106, and an examination start button 107.

Examinations received from the RIS 12 are aligned and displayed as a list on the requested examination list 103. When one of the examinations is selected from the requested examination list 103, patient information (patient ID, patient name, date of birth, etc.) corresponding to the selected patient is displayed in the patient information display region 104 as shown in FIG. 2B. An examination ID is displayed in the imaging information display region 105, and imaging information corresponding to the examination ID is displayed immediately below this region. As described above, the imaging information is received from the RIS 12. Imaging method buttons 109 (a front-of-chest button 109a and a side-of-chest button 109b) corresponding to the respective pieces of imaging information are arranged in the examples of FIGS. 2A to 2C. As shown in FIG. 2C, an imaging information input region 108 can be displayed, in accordance with the pressing of the imaging information input button 106, to further add an imaging method. In the example of FIG. 2C, a plurality of imaging method selection buttons 114 are displayed in the imaging information input region 108. An imaging method can be added by selecting one of these buttons. Each added imaging method is aligned and displayed in association with the front-of-chest button 109a and the side-of-chest button 109b in the imaging information display region 105. Each imaging method is associated with an imaging method ID.

The operator presses the examination start button 107 after confirming the patient information and the imaging information. This confirms the examination to be performed. In accordance with the pressing of the examination start button 107, the radiation imaging control apparatus 1 displays an imaging screen as that shown in each of the FIGS. 3A and 3B in the display unit 2. The imaging screen is a screen used during imaging.

Figure 3A:
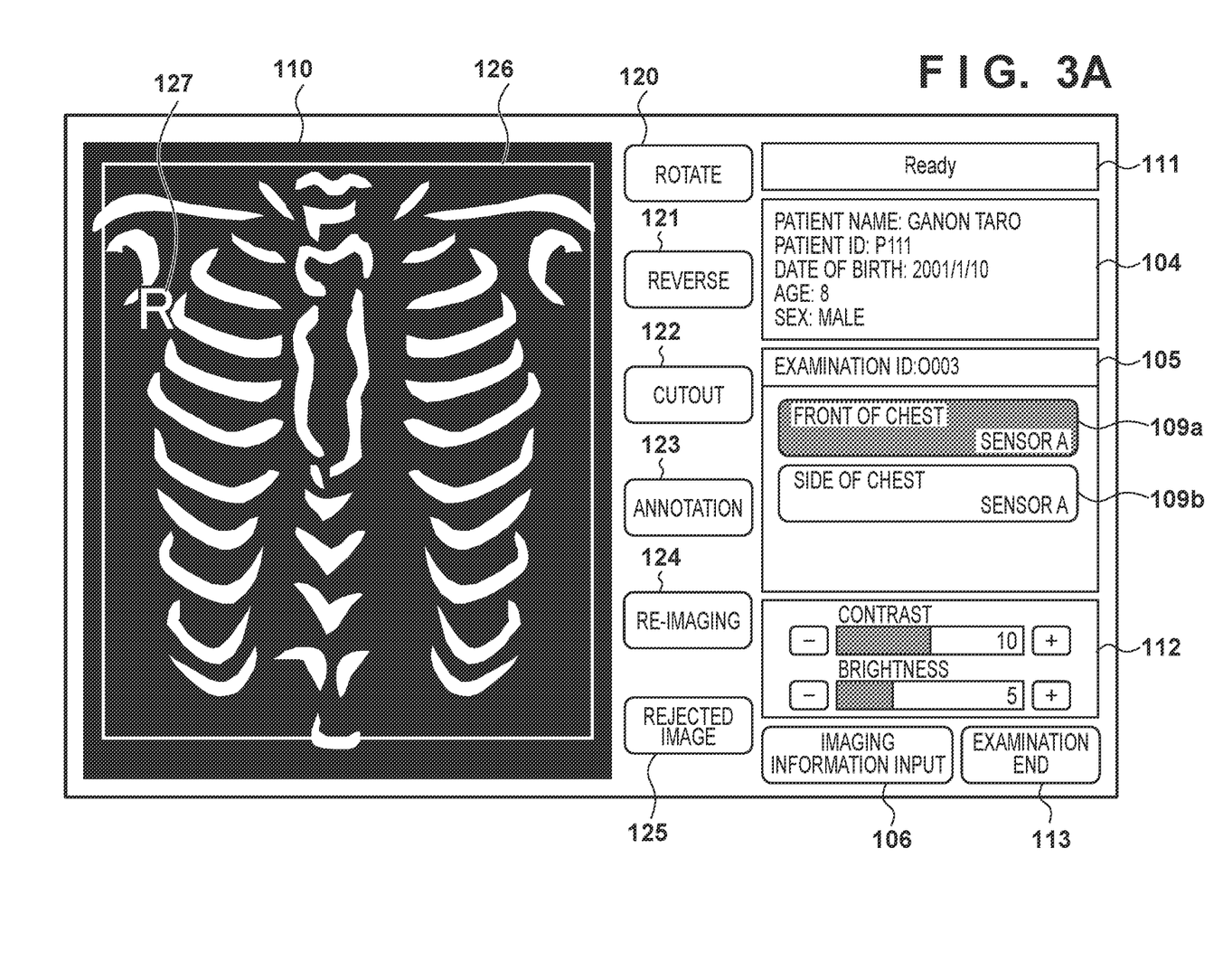
FIGS. 3A and 3B are views each showing an example of an imaging screen according to the embodiment of the present invention.
Figure 3B:
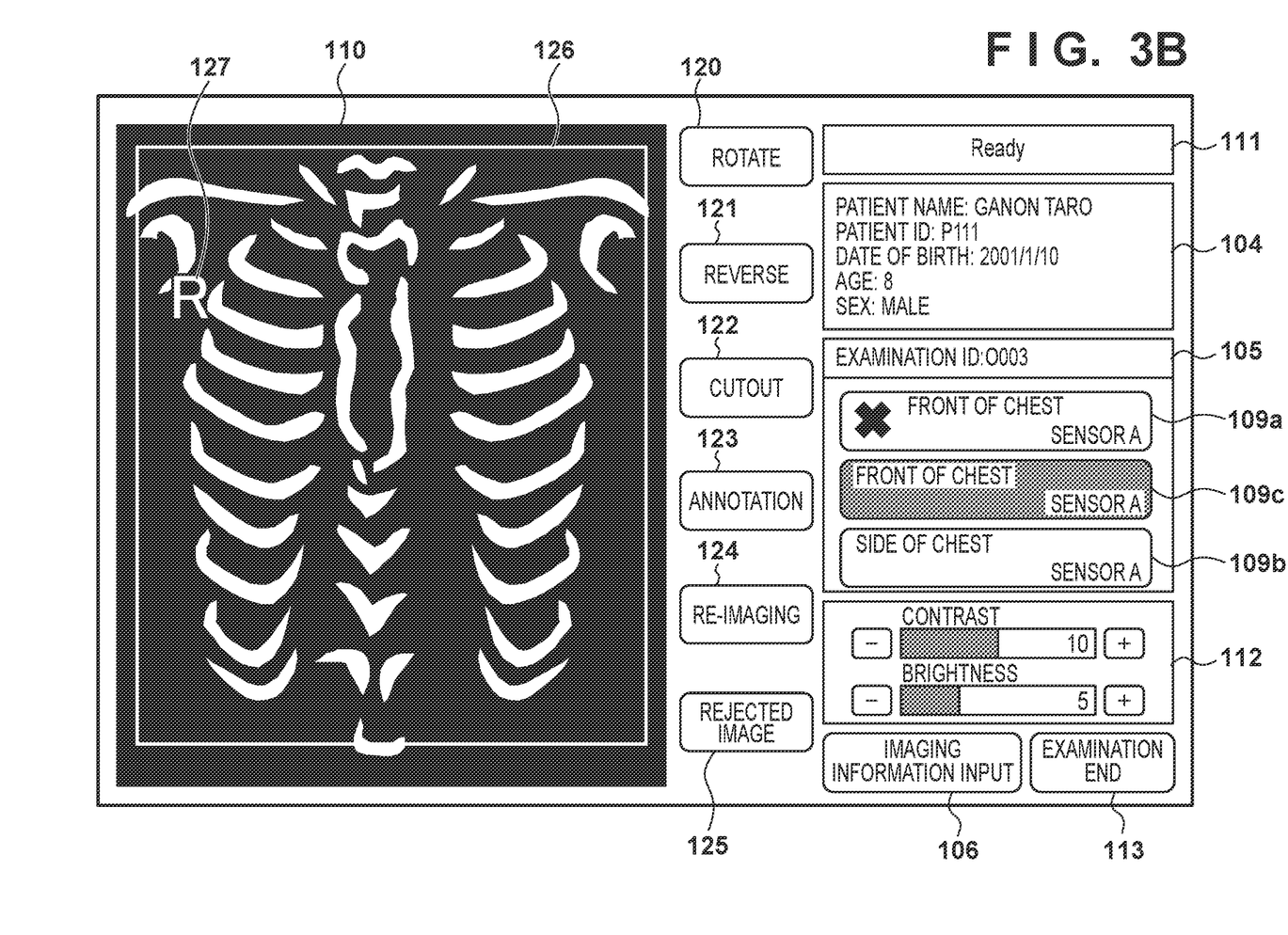

The imaging screen is configured to basically include the same display regions as those described in the new examination input screen in FIGS. 2A to 2C. As shown in FIGS. 3A and 3B, the display regions that are to be newly added are a screen display region 110, a message region 111, an image processing setting region 112, and an examination end button 113.

When the imaging screen is displayed, the imaging method button 109a which is arranged in the uppermost portion in the imaging information display region 105 is in a selected state by default. Along with this, the imaging control unit 5 of the radiation imaging control apparatus 1 transmits, to the radiation generation control unit 4, the imaging conditions (tube voltage, tube current, and irradiation time) set in correspondence with the imaging method button (imaging method). The imaging control unit 5 then controls the radiation detector 7 in accordance with the imaging conditions to prepare for imaging.

When the preparation is complete, the radiation imaging control apparatus 1 changes to an imaging enable state. At this time, a "Ready message" indicating the imaging enable state is displayed in the message region 111.

Next, the operator confirms the imaging method, performs imaging settings, and performs positioning of the patient. When a series of imaging preparation operations has been completed, the operator presses a radiation irradiation switch (not shown) after confirming the imaging enable state by referring to the message region 111. The radiation imaging control apparatus 1 accordingly irradiates the object (specific portion of the patient) with radiation from the radiation generation unit 8 and causes the radiation detector 7 to detect the radiation transmitted through the object. As a result, a radiation image is captured.

After imaging is complete, the imaging control unit 5 of the radiation imaging control apparatus 1 obtains the captured image from the radiation detector 7 and performs image processing on the obtained captured image based on predetermined image processing conditions. The predetermined imaging conditions are predefined in correspondence with the imaging method.

When the image processing ends, the radiation imaging control apparatus 1 displays the image-processed-captured image in the screen display region 110. If the operator wants to change, for example, the contrast of the captured image, he/she can operate a button for contrast or brightness provided in the image processing setting region 112.

In the same manner, if the operator wants to change the cutout region of an output image, he/she can operate a cutout button 122 and a cutout frame 126 to designate the desired cutout region. When a character string which is to serve as diagnostic information is to be added, an annotation button 123 is operated to superimpose a character string on an image as shown by an annotation 127. If the orientation of the image is not suitable for diagnosis, a rotate button 120 and a reverse button 121 are used to perform geometric conversion. As described above, the operator can perform additional image editing to the captured image displayed in the screen display region 110.

If the operator determines that the imaging has failed, re-imaging can be performed by pressing a re-imaging button 124. When the re-imaging button 124 is pressed, an imaging method button 109c which is the same as that of the re-imaging target is added to the imaging information display region 105 as shown in FIG. 3B, and the imaging control unit 5 prepares for imaging by controlling the radiation detector 7 in accordance with the imaging conditions. The image that became an imaging target is handled as a rejected image. An icon is displayed on the imaging method button 109a to indicate that it is a rejected image.

As DICOM (Digital Imaging and Communication in Medicine) additional information, the same series ID as that of the re-imaging target image is added to the re-captured image. If a rejected image button 125 is pressed, the captured image is handled as a rejected image without performing re-imaging. Note that if the operator presses an imaging method button 109 whose imaging operation has not been performed yet, the imaging conditions and the image processing conditions of the current image are stored and the next imaging is started.

The operator performs imaging by all of the imaging methods in the imaging information display region 105 by repeating the aforementioned procedure. When all of the imaging operations are finished, the operator presses the examination end button 113. This causes the series of examinations to end, and the radiation imaging control apparatus 1 displays the new examination input screen again. At this time, the radiation imaging control apparatus 1 adds the examination information and the imaging information as additional information to each diagnostic image which is not handled as a rejected image in the imaging control unit 5 and outputs the diagnostic image with the additional information to, for example, the PACS 13, the printer 14, and the ROM in the self-apparatus. In addition, the imaging control unit 5 outputs each rejected image and the corresponding diagnostic image to be used for comparison in its analysis to the rejected image analysis system 17. Note that the captured image and the patient information are associated and stored in the RIS 12 and the ROM.

<Extraction Method of Diagnostic Image>

Figure 4:
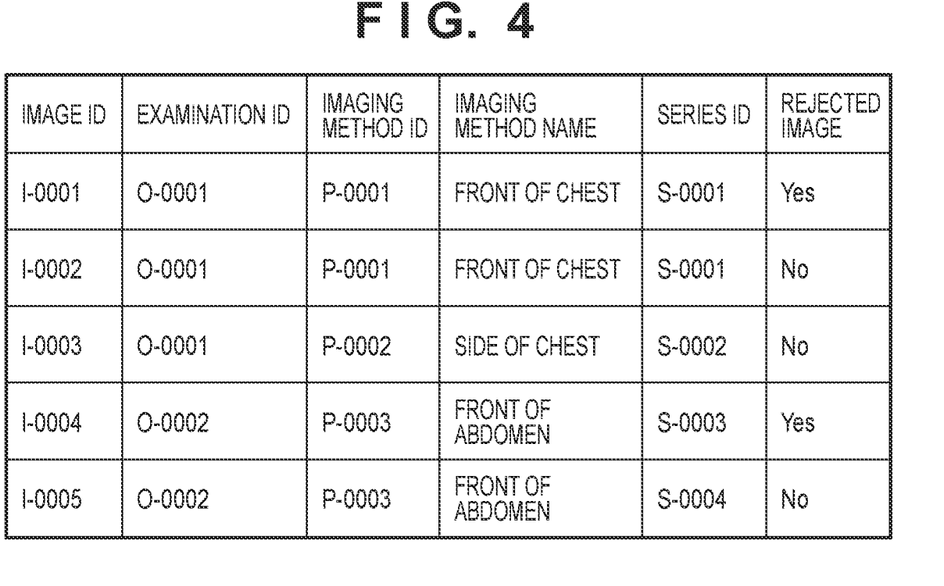
FIG. 4 is a view showing an example of an image information table according to the embodiment of the present invention.

An extraction method of the diagnostic image for comparison will be described next. The information of the captured image is, for example, stored in a database as an image information table shown in FIG. 4. The image information table includes an image ID, an examination ID, an imaging method ID, an imaging method name, a series ID as DICOM additional information, and rejected image information. The imaging control unit 5 of the radiation imaging control apparatus 1 extracts a rejected image I-0001 in the output processing of an examination ID O-0001. Additionally, an image I-0002 having the same series ID as the rejected image I-0001 is extracted as the diagnostic image for comparison. Alternatively, as in the case of images I-0004 and I-0005 having an examination ID O-0002, images having the same imaging method ID or images of the same examination are extracted as the rejected image and the diagnostic image for comparison.

In addition, a standard image may be held in the imaging control unit 5 for each imaging method in advance, and a standard image having the same imaging method ID may be extracted as the diagnostic image for comparison with the rejected image. The list of images stored in the image information table shown in FIG. 4 may be displayed on the display unit 2, and the operator may select the diagnostic image for comparison. That is, a diagnostic image for comparison corresponding to the rejected image may be extracted based on user selection.

<Generation Processing of Diagnostic Image for Comparison>

Figure 5:
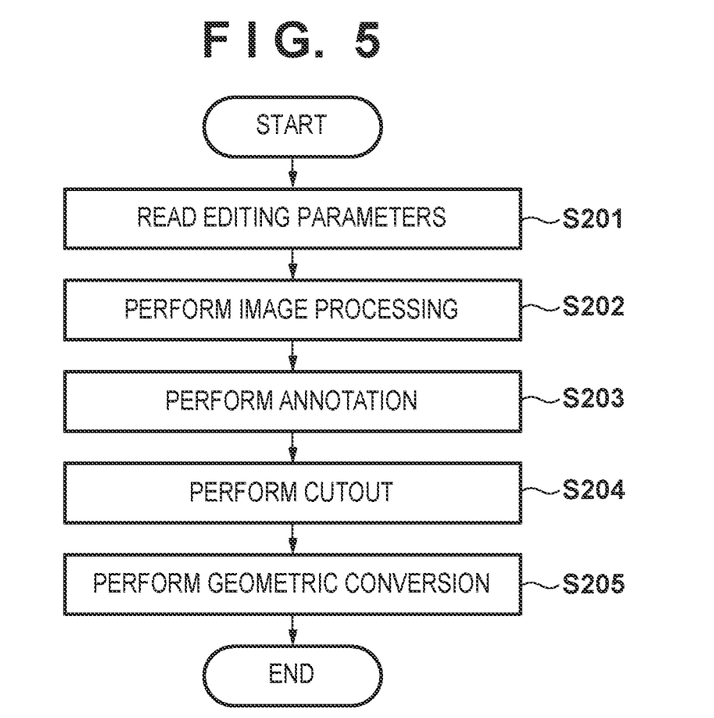
FIG. 5 is a flowchart showing a procedure of processing according to the embodiment of the present invention.
Figure 6:
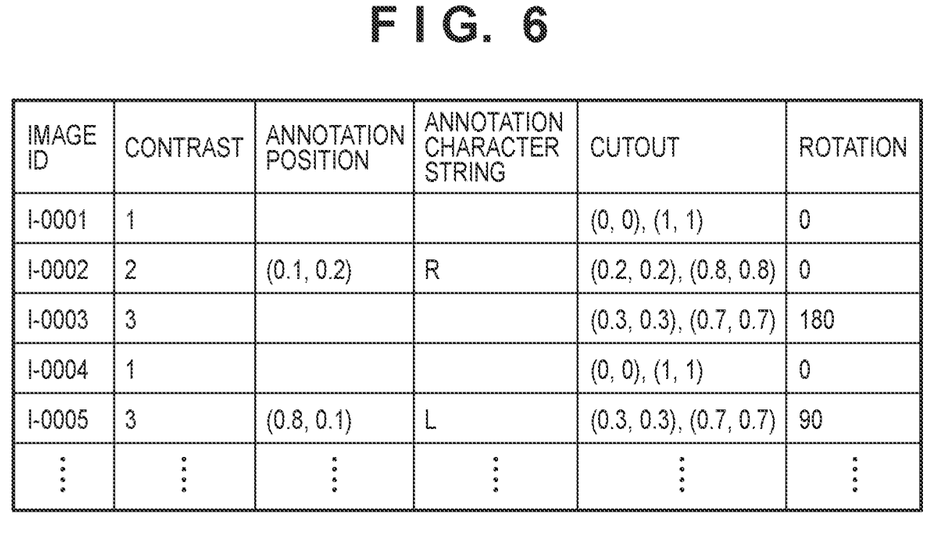
FIG. 6 is a view showing an example of an image editing information table according the embodiment of the present invention.

A generation processing procedure of a diagnostic image for comparison will be described next with reference to the flowchart shown in FIG. 5. In step S201, the imaging control unit 5 reads an editing parameter to be performed on an output image. The aforementioned image editing information is stored in, for example, a database as an image editing information table as shown in FIG. 6. The image editing information table includes an image processing parameter such as the contrast, relative coordinates indicating the upper left and lower right portions of a cutout region, relative coordinates indicating an annotation position, an annotation character string, and a rotation angle. For example, if the image I-0002 is to be output as a diagnostic image, the data belonging to the row of I-0002 is read from the image editing information table.

Next, the imaging control unit 5 sequentially performs image processing in step S202, annotation embedding processing in step S203, cutout processing in step S204, and geometric conversion processing in step S205, and an output image is generated as a result.

Here, if the output image is a diagnostic image for comparison with a rejected image, an editing parameter of the rejected image is read in step S201. For example, if the image I-0002 is to be output as the diagnostic image for comparison with a rejected image, the editing parameter of the image I-0001 which is a rejected image is read. Subsequently, a diagnostic image for comparison to which image editing has been performed using the same editing conditions as the rejected image is generated by performing the processes of steps S202, S203, S204, and S205. The imaging control unit 5 outputs the rejected image and the diagnostic image for comparison to the rejected image analysis system 17.

Note that concerning the annotation embedded in step S203, a case in which an annotation is added to only the rejected image as supplementary information for the rejected image analysis can be considered. In this case, the information of the image I-0002 serving as the diagnostic image for comparison can be read as annotation editing information of the diagnostic image for comparison, and the information of the image I-0001 as the rejected image can be read for other pieces of editing information in the reading operation of step S201.

According to the present invention, a technique for collecting a rejected image and a diagnostic image for comparison suitable for a rejected image analysis can be provided. In addition, since a diagnostic image has undergone processing for diagnostic support purposes, a diagnostic image may not be suitable for comparison with a rejected image. However, according to the present invention, it is possible to collect an image suitable for the rejected image analysis since an image that has undergone the same processing is output.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-083854, filed Apr. 19, 2016, which is hereby incorporated by reference wherein in its entirety.

What is claimed is:
1. A radiation imaging control apparatus, comprising:
an obtainment unit configured to obtain a radiation image captured by an image capturing unit;
an extraction unit configured, in a case where the radiation image captured by the image capturing obtainment unit is a rejected image related to a failed imaging, to extract the rejected image, a diagnostic image and an image for comparison corresponding to the rejected image from a plurality of radiation images; and
an output unit configured to output the diagnostic image to a first external device and to output the rejected image and the image for comparison to a second external apparatus, wherein
the diagnostic image is an image not identified as the rejected image, and
the rejected image and the image for comparison are images processed with a common parameter.
2. The apparatus according to claim 1, further comprising an input unit configured to accept an input that the radiation image captured by the image capturing unit is the rejected image, wherein the image capturing unit re-captures the radiation image in accordance with the input by the input unit.

3. The apparatus according to claim 2, wherein the extraction unit extracts a radiation image with an imaging method ID the same as the rejected image as the image for comparison.

4. The apparatus according to claim 2, wherein the extraction unit extracts a radiation image belonging to an examination the same as the rejected image as the image for comparison.

5. The apparatus according to claim 2, wherein the extraction unit extracts a standard image having an imaging method ID the same as the rejected image from standard images held in advance for respective imaging methods as the image for comparison.

6. The apparatus according to claim 2, wherein the extraction unit extracts the image for comparison corresponding to the rejected image based on user selection.

7. The apparatus according to claim 1, further comprising an editing unit configured to edit the radiation image captured by the image capturing unit, wherein
the output unit outputs to the external apparatus the rejected image and image for comparison edited with a same editing condition.

8. The apparatus according to claim 7, wherein the extraction unit extracts a radiation image with an imaging method ID the same as the rejected image as the image for comparison.

9. The apparatus according to claim 7, wherein the extraction unit extracts a radiation image belonging to an examination the same as the rejected image as the image for comparison.

10. The apparatus according to claim 7, wherein the extraction unit extracts a standard image having an imaging method ID the same as the rejected image from standard images held in advance for respective imaging methods as the image for comparison.

11. The apparatus according to claim 7, wherein the extraction unit extracts the image for comparison corresponding to the rejected image based on user selection.

12. The apparatus according to claim 1, wherein the extraction unit extracts a radiation image with a series ID the same as the rejected image as the image for comparison.

13. The apparatus according to claim 12, wherein the series ID is DICOM additional information.

14. The apparatus according to claim 1, wherein the extraction unit extracts a radiation image with an imaging method ID the same as the rejected image as the image for comparison.

15. The apparatus according to claim 1, wherein the extraction unit extracts a radiation image belonging to an examination the same as the rejected image as the image for comparison.

16. The apparatus according to claim 1, wherein the extraction unit extracts a standard image having an imaging method ID the same as the rejected image from standard images held in advance for respective imaging methods as the image for comparison.

17. The apparatus according to claim 1, wherein the extraction unit extracts the image for comparison corresponding to the rejected image based on user selection.

18. The radiation imaging control apparatus according to claim 1, wherein the diagnostic image also serves as the image for comparison.

19. A method of controlling a radiation imaging control apparatus, comprising:
obtaining a radiation image captured by an image capturing unit;
extracting, in a case where the radiation image captured by the image capturing unit is a rejected image related to a failed image, the rejected image, a diagnostic image and an image for comparison corresponding to the rejected image from a plurality of radiation images; and
outputting the diagnostic image to a first external device and outputting the rejected image and the image for comparison to a second external apparatus, wherein
the diagnostic image is an image not identified as the rejected image, and
the rejected image and the image for comparison are images processed with a common parameter.

20. A non-transitory computer-readable storage medium storing a computer program for causing a computer to execute each step of a method of controlling a radiation imaging control apparatus, the method comprising:
obtaining a radiation image captured by an image capturing unit;
extracting, in a case where the radiation image captured by the image capturing unit is a rejected image related to a failed image, the rejected image, a diagnostic image and an image for comparison corresponding to the rejected image from a plurality of radiation images; and
outputting the diagnostic image to a first external device and outputting the rejected image and the image for comparison to a second external apparatus, wherein
the diagnostic image is an image not identified as the rejected image, and
the rejected image and the image for comparison are images processed with a common parameter.

21. The non-transitory computer-readable storage medium according to claim 20, wherein the diagnostic image is the image for comparison.

* * * * *